US011642356B2

(12) United States Patent
Hull et al.

(10) Patent No.: US 11,642,356 B2
(45) Date of Patent: May 9, 2023

(54) PHARMACEUTICAL COMPOSITIONS

(71) Applicants: Wade Hull, Kaysville, UT (US); Ngoc Truc-Chi Vo, Longueuil (CA); Dominic King-Smith, San Diego, CA (US)

(72) Inventors: Wade Hull, Kaysville, UT (US); Ngoc Truc-Chi Vo, Longueuil (CA); Dominic King-Smith, San Diego, CA (US)

(73) Assignee: Crescita Therapeutics Inc., Mississauga (CA)

(*) Notice: Subject to any disclaimer, the term of this patent is extended or adjusted under 35 U.S.C. 154(b) by 363 days.

(21) Appl. No.: 16/343,690

(22) PCT Filed: Oct. 21, 2016

(86) PCT No.: PCT/US2016/058240
§ 371 (c)(1),
(2) Date: Apr. 19, 2019

(87) PCT Pub. No.: WO2018/075071
PCT Pub. Date: Apr. 26, 2018

(65) Prior Publication Data
US 2019/0255070 A1    Aug. 22, 2019

(51) Int. Cl.
*A61K 31/573*    (2006.01)
*A61K 9/08*    (2006.01)
(Continued)

(52) U.S. Cl.
CPC .......... *A61K 31/573* (2013.01); *A61K 9/0014* (2013.01); *A61K 9/08* (2013.01);
(Continued)

(58) Field of Classification Search
CPC ...... A61K 31/573; A61K 47/12; A61K 47/14; A61K 9/0014; A61P 17/06
See application file for complete search history.

(56) References Cited

U.S. PATENT DOCUMENTS

2008/0004246 A1    1/2008  Bodor
2011/0207765 A1*   8/2011  Van Den Bussche .. A61P 37/02
                                                            514/292
(Continued)

FOREIGN PATENT DOCUMENTS

WO    WO 2015/044857 A    4/2015

OTHER PUBLICATIONS

PCT Application No. PCT/US16/58240 Filing Date Oct. 21, 2016; Wade Hull, International Search Report dated Mar. 3, 2017; 9 Pages.

*Primary Examiner* — Savitha M Rao
*Assistant Examiner* — Andrew P Lee
(74) *Attorney, Agent, or Firm* — Thorpe North & Western, LLP

(57) ABSTRACT

In one example presented herein, is a pharmaceutical composition. The pharmaceutical composition can include halobetasol propionate, from 0 wt % to 3 wt % ethoxylated castor oil, a first compound, and a second compound. The first compound and the second compound can be selected from; N-lauroyl sarcosine, sodium octyl sulfate, methyl laurate, isopropyl myristate, oleic acid, glyceryl oleate, and sodium lauryl sulfoacetate. The first compound and the second compound are not the same.

11 Claims, 1 Drawing Sheet

(51) Int. Cl.
 *A61K 47/12* (2006.01)
 *A61K 47/14* (2017.01)
 *A61P 17/06* (2006.01)
 *A61K 9/00* (2006.01)

(52) U.S. Cl.
 CPC .............. *A61K 47/12* (2013.01); *A61K 47/14* (2013.01); *A61P 17/06* (2018.01)

(56) References Cited

U.S. PATENT DOCUMENTS

| | | | |
|---|---|---|---|
| 2012/0214776 A1* | 8/2012 | Ubaidulla | A61K 31/573 514/174 |
| 2012/0214778 A1 | 8/2012 | Dimery et al. | |
| 2014/0255521 A1* | 9/2014 | Lozinsky | A61P 1/00 424/725 |
| 2015/0297723 A1* | 10/2015 | Kisak | A61K 31/245 514/179 |

* cited by examiner

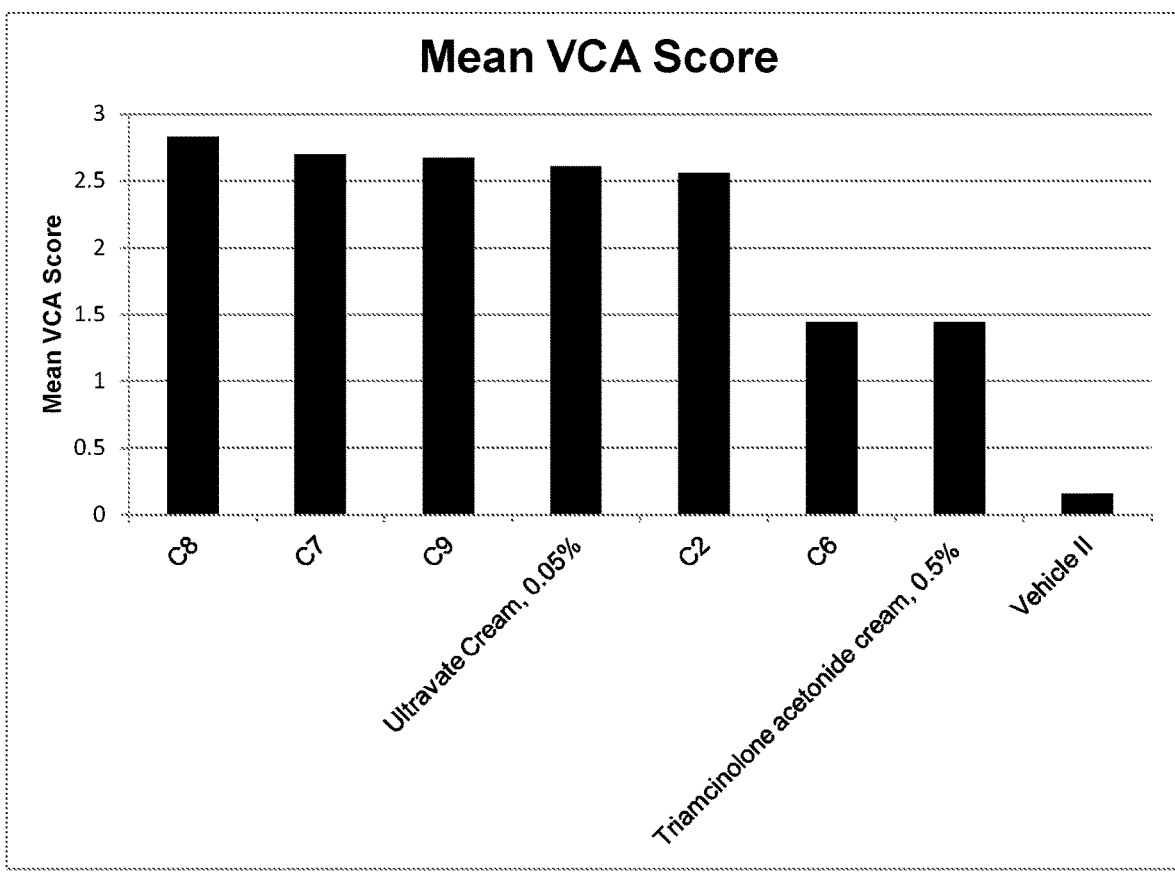

PHARMACEUTICAL COMPOSITIONS

BACKGROUND

Compositions for topical application can be useful in treating cosmetic conditions, medical conditions, or in applying an active agent to numb underlying tissues. Topical application can be desirable because it can allow for an active agent to be applied directly to the site of interest, avoid gastrointestinal absorption, avoid first-pass metabolism, and allow for delivery of active agents that have a relatively short biological half-life and/or a narrow therapeutic window.

Despite these advantages, formulating compositions for topical application can be challenging because of the structural composition of skin. Skin consists of two principal parts, namely (i) the epidermis (outermost layer) and (ii) the dermis (innermost layer). The outermost layer of the epidermis (stratum corneum) consists of corneocytes (aggregated keratin filaments encased in a cornified envelope) that are surrounded by extracellular lipids. The lipids are arranged as multiple lamellar bilayers and their arrangement can block entry of topically applied drugs into the skin.

Delivering an active agent topically into or through the skin can involve reducing the stratum corneum's barrier properties. One method of reducing the stratum corneum's barrier includes formulating a composition with molecular penetration enhancers (MPE) or chemical penetration enhancers. These enhancers can disrupt the lipid bilayers of the stratum corneum; thereby, allowing active agent(s) to penetrate or cross the lipid bilayers of the stratum corneum.

Over 300 substances have been identified as excipients for drug products. Despite this, very few of these substances have been successfully incorporated into commercial formulations. Many excipients are irritating to the cells of the epidermis which can limit both the choice and concentration of the excipient suitable for topical formulation. Other excipients can have a negative impact on the stability of the formulation, for example, changing the pH of the composition over time, degrading the active component of the formulation, or can cause compatibility issues with other ingredients. These factors can impact the product's efficacy, shelf life, and administration regimen. Thus, there is a need to develop new topical formulations with improved stability and drug delivery.

SUMMARY

The present disclosure is drawn to pharmaceutical compositions and methods of treating a skin condition. In one example, the present disclosure is drawn to a pharmaceutical composition that can include an active such as halobetasol propionate, from 0 wt % to 3 wt % ethoxylated castor oil, a first compound, and a second compound. The first compound and the second compound can each be, independently, N-lauroyl sarcosine, sodium octyl sulfate, methyl laurate, isopropyl myristate, oleic acid, glyceryl oleate, or sodium lauryl sulfoacetate. The first compound and the second compound are not the same.

In another example, a pharmaceutical composition can include an active such as halobetasol propionate, a first compound, and a second compound. In one example, the first compound can be methyl laurate and the second compound can be oleic acid. In another example, the first compound can be sodium lauryl sulfoacetate and the second compound can be isopropyl myristate. In yet another example, the first compound can be sodium lauryl sulfoacetate and the second compound can be oleic acid. The pharmaceutical composition can include from 0 wt % to 3 wt % ethoxylated castor oil, or in one example, can be devoid of ethoxylated castor oil.

In another example, a method of treating a skin condition can include applying a pharmaceutical composition to a skin surface at a site of the skin condition. The pharmaceutical composition can include an active such as halobetasol propionate, from 0 wt % to 3 wt % ethoxylated castor oil, a first compound, and a second compound. The first compound and the second compound can each be, independently, N-lauroyl sarcosine, sodium octyl sulfate, methyl laurate, isopropyl myristate, oleic acid, glyceryl oleate, or sodium lauryl sulfoacetate. The first compound and the second compound are not the same. In certain specific examples, the first compound can be methyl laurate and the second compound can be oleic acid. In another example, the first compound can be sodium lauryl sulfoacetate and the second compound can be isopropyl myristate. In yet another example, the first compound can be sodium lauryl sulfoacetate and the second compound can be oleic acid. In these and other examples, in certain embodiments, the pharmaceutical composition can be devoid of ethoxylated castor oil.

In yet another example, a pharmaceutical composition is presented. The pharmaceutical composition can include halobetasol propionate, diisopropyl adipate, hexylene glycol, methyl laurate, and oleic acid.

BRIEF DESCRIPTION OF THE DRAWINGS

Reference will now be made to the exemplary embodiments illustrated, and specific language will be used herein to describe the same. It will nevertheless be understood that no limitation of the scope of the invention is thereby intended.

FIG. 1 is a plot of the vasoconstriction assay (VCA) scores for several exemplary embodiments of formulations disclosed herein and two commercially available formulations (i.e., Ultravate® cream (Ranbaxy) and Triamcinolone acetonide cream (E. Fougera & Co.).

DETAILED DESCRIPTION

Before particular embodiments of the present invention are disclosed and described, it is to be understood that this invention is not limited to the particular process and materials disclosed herein as such may vary to some degree. It is also to be understood that the terminology used herein is used for the purpose of describing particular embodiments only and is not intended to be limiting, as the scope of the present invention will be defined only by the appended claims and equivalents thereof.

In the present disclosure, the following terminology will be used.

The singular forms "a," "an," and "the" include plural referents unless the context clearly dictates otherwise. Thus, for example, reference to "a solvent" includes reference to one or more solvent(s).

As used herein, "comprises," "comprising," "containing," "including" and "having" and the like can have the meaning ascribed to them in U.S. Patent law and can mean "includes," "including," and the like, and are generally interpreted to be open ended terms. The terms "consisting of" or "consists of" are closed terms, and include only the components, structures, steps, or the like specifically listed in conjunction with such terms, as well as that which is in accordance with U.S. Patent law. "Consisting essentially of"

or "consists essentially of" have the meaning generally ascribed to them by U.S. Patent law. In particular, such terms are generally closed terms, with the exception of allowing inclusion of additional items, materials, components, steps, or elements, that do not materially affect the basic and novel characteristics or function of the item(s) used in connection therewith. For example, trace elements present in a composition, but not affecting the composition's nature or characteristics would be permissible if present under the "consisting essentially of" language, even though not expressly recited in a list of items following such terminology. When using an open ended term in the written description, like "comprising" or "including," it is understood that direct support should be afforded also to "consisting essentially of" language, as well as, "consisting of" language as if stated explicitly, and vice versa.

As used herein the term "ethoxylated castor oil" refers to polyoxyl n castor oil (n=30 to 40), including polyoxyl 35 castor oil (also known as Cremophor EL).

As used herein, the term "comparative formulation" is a formulation that is compositionally identical with the exception that amounts (wt %) of the identified compound is replaced with the same amount (wt %) of water, or vice versa (where water replaces the omitted compound). Thus, for example, a comparable formulation may not include a "first compound" and a "second compound" for comparison purposes, where these ingredients are replaced with the same wt % water.

"Multiplexed molecular penetration enhancers" (MMPE) as described herein include N-lauroyl sarcosine, sodium octyl sulfate, methyl laurate, isopropyl myristate, oleic acid, glyceryl oleate, or sodium lauryl sulfoacetate, and in accordance with examples described herein, typically they are used in combination, e.g., two or more. The use of a permeation enhancer(s) can be incorporated in a topical formulation to facilitate administration of one or more active ingredients, including halobetasol propionate.

The term "penetration enhancer" is used herein to refer to an agent that improves the transport of molecules such as an active agent (e.g., halobetasol propionate) into or through the skin. Various conditions may occur at different sites in the body either in the skin or below creating a need to target delivery of compounds. For example, a psoriasis treatment may benefit from delivery of therapeutic drug levels into the deeper tissue. A "penetration enhancer" may be used to assist in the delivery of an active agent directly to the skin or underlying tissue or indirectly to the site of the disease through systemic distribution. A penetration enhancer may be a pure substance or may comprise a mixture of different chemical entities. In the present disclosure, the terms "penetration enhancer," "chemical penetration enhancer," "multiplexed molecular penetration enhancer," and "MMPE" can often be used interchangeably unless the context dictates otherwise. As an example, discussion of a generic penetration enhancer or a ethoxylated castor oil penetration enhancer does not refer specifically to the MMPE penetration enhancer compositions described herein.

"Skin" is defined to include human skin (intact, diseased, ulcerous, or broken) as well as mucosal surfaces that are usually at least partially exposed to air such as lips, genital and anal mucosa, and nasal and oral mucosa.

As used herein, the term "skin contact region" refers to an area wherein the topical formulation contacts the skin.

The term "subject" as used herein includes all members of the animal kingdom, including mammals, and most typically, refers to humans.

The term "topical administration" is used in its conventional sense to mean delivery of a substance, such as a therapeutically active agent, into the skin or a localized region of the body. Topical administration of a drug may often be advantageously applied in, for example, the treatment of various skin disorders or conditions.

As used herein the term "topical formulation," or "pharmaceutical composition" can be used interchangeably and refers to a formulation that may be applied to skin or a mucosa. Topical formulations may, for example, be used to confer therapeutic benefit to a patient or cosmetic benefits to a consumer. Topical formulations can be used for both topical and transdermal administration of substances.

As used herein, the term "transdermal" means in the broadest sense into or through the skin. Further the terms "transdermal" and "percutaneous" are used interchangeably throughout this specification.

The term "transdermal administration" is used to mean administration through the skin. Transdermal administration is often applied where systemic delivery of an active is desired, although it may also be useful for delivering an active to tissues underlying the skin with minimal systemic absorption (i.e. localized delivery).

The term "treating" or "treatment" as used herein and as is well understood, and includes an approach for obtaining beneficial or desired results, including clinical results. Beneficial or desired clinical results can include, but are not limited to, alleviation or amelioration of one or more symptoms or conditions, diminishment of extent of disease, stabilizing (i.e. not worsening) the state of disease, delaying or slowing of disease progression, amelioration or palliation of the disease state, diminishment of the reoccurrence of disease, and remission (whether partial or total), whether detectable or undetectable. In addition to being useful as methods of treatment, the methods described herein may be useful for the prevention or prophylaxis of disease.

The term "water" as an ingredient in the pharmaceutical compositions of the present disclosure can refer to pharmaceutically-acceptable water.

As used herein, the term "about" is used to provide flexibility to a numerical range endpoint by providing that a given value may be "a little above" or "a little below" the endpoint. The degree of flexibility of this term can be dictated by the particular variable and would be within the knowledge of those skilled in the art to determine based on experience and the associated description herein. For example, the degree of flexibility can be within about ±2%, ±1%, or ±0.05%, of the numerical value.

As used herein, a plurality of active agents and/or compounds may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 0.01 mm to 2.0 mm" should be interpreted to include not only the explicitly recited values of about 0.01 mm to about 2.0 mm, but also include individual values and sub-ranges within the indicated range. Thus, included in this numerical range are individual values such as 0.5 mm, 0.7 mm, and 1.5 mm, and sub-ranges such as from 0.5 mm to 1.7 mm, 0.7 mm to 1.5 mm, and from 1.0 mm to 1.5 mm, etc. Furthermore, such an interpretation should apply regardless of the breadth of the range or the characteristics being described. Additionally, it is noted that all percentages are in weight, unless specified otherwise.

In one example, a pharmaceutical composition can include an active agent, such as halobetasol propionate, from about 0 wt % to about 3 wt % ethoxylated castor oil, a first compound, and a second compound. The first compound and the second compound can each be, independently, N-lauroyl sarcosine, sodium octyl sulfate, methyl laurate, isopropyl myristate, oleic acid, glyceryl oleate, or sodium lauryl sulfoacetate. Thus, the first compound and the second compound are not the same.

In another example, a pharmaceutical composition can include an active agent, such as halobetasol propionate, a first compound, and a second compound. In one example, the first compound can be methyl laurate and the second compound can be oleic acid. In another example, the first compound can be sodium lauryl sulfoacetate and the second compound can be isopropyl myristate. In yet another example, the first compound can be sodium lauryl sulfoacetate and the second compound can be oleic acid. The pharmaceutical composition can include from 0 wt % to 3 wt % ethoxylated castor oil, or in one example, can be devoid of ethoxylated castor oil.

In another example, a method of treating a skin condition can include applying a pharmaceutical composition to a skin surface at a site of the skin condition. The pharmaceutical composition can include an active agent, such as halobetasol propionate, from 0 wt % to 3 wt % ethoxylated castor oil, a first compound, and a second compound. The first compound and the second compound can each be, independently, N-lauroyl sarcosine, sodium octyl sulfate, methyl laurate, isopropyl myristate, oleic acid, glyceryl oleate, or sodium lauryl sulfoacetate. In certain specific examples, the first compound can be methyl laurate and the second compound can be oleic acid. In another example, the first compound can be sodium lauryl sulfoacetate and the second compound can be isopropyl myristate. In yet another example, the first compound can be sodium lauryl sulfoacetate and the second compound can be oleic acid. In these and other examples, in certain embodiments, the pharmaceutical composition can be devoid of ethoxylated castor oil.

In another example, the pharmaceutical composition can include halobetasol propionate, diisopropyl adipate, hexylene glycol, methyl laurate, and oleic acid. The pharmaceutical composition can further include isopropyl alcohol, water, and buffers. Non-limiting examples of buffers include citric acid (anhydrous) and sodium citrate, dihydrate.

Turning now to the active agent, the active agent can be any of the active agents identified in U.S. Pat. No. 8,343,962 and U.S. Pub. No. 2015/0297723, which are specifically incorporated herein by reference. In another example, such as in the many examples herein, the active agent can be halobetasol propionate. Halobetasol propionate is an active agent that can be used to treat various skin conditions. This active agent is classified as a corticosteroid and has the molecular formula $C_{25}H_{31}ClF_2O_5$. The chemical structure of halobetasol propionate is shown in Formulation I, as follows:

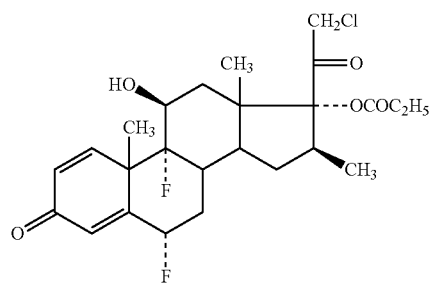

Formulation I

Topical corticosteroids can induce vasoconstriction when applied to a skin surface. The induced vasoconstriction can be utilized to gauge the potency of topical corticosteroids by, for example, measuring color changes in the skin either visually or mechanically by means of a chromameter. The potency of a topical corticosteroid formulation in general depends on many factors including the identity of the active ingredient, the concentration of the active ingredient, and the excipients incorporated into the formulation. In some examples, corticosteroids can be classified according to their potency and the degree of vasoconstriction they cause. Halobetasol propionate is classified in the highest potency category of corticosteroids.

In one example, the halobetasol propionate in the pharmaceutical composition can range from about 0.01 wt % to about 10 wt %. In another example, the halobetasol propionate can be present from about 0.01 wt % to about 5 wt %. In yet another example, the halobetasol propionate can be present from about 0.01 wt % to about 2 wt %. In a further example, the halobetasol propionate can range from about 0.025 wt % to about 1 wt %. In yet another example, the halobetasol propionate can be present at about 0.25 wt % to about 2 wt %. In one example, the halobetasol propionate can be present at about 0.05 wt %.

In some examples, the pharmaceutical composition can also include either no ethoxylated castor oil, or small amounts of ethoxylated castor oil, e.g., up to 3 wt %, up to 2 wt %, up to 1 wt %, up to 0.5 wt %, or up to 0.1 wt %. Ethoxylated castor oil, such as polyoxyl 35 castor oil, is a non-ionic surfactant. Ethoxylated castor oil may generally be incorporated into compositions as an emulsifying or solubilizing agent and is generally known to improve the solubilization of lipophilic drugs in oral, topical, parenteral, and cosmetic formulations. Typically, ethoxylated castor oil is known to act as a hydrophilic penetration enhancer, making it surprising that its inclusion in certain formulations described herein actually hindered its topical potency properties.

In accordance with this application, the pharmaceutical composition can include from about 0 wt % to about 3 wt % ethoxylated castor oil. In another example, the pharmaceutical composition can include from about 0.01 wt % to about 3 wt % ethoxylated castor oil. In yet another example, the pharmaceutical composition can include from about 0.01 wt % to about 1 wt % ethoxylated castor oil. In a further example, the pharmaceutical composition can be substantially devoid of ethoxylated castor oil, i.e. contain about 0 wt % ethoxylated castor oil allowing for trace amounts less than 0.01 wt %, or being completely devoid of ethoxylated castor oil. In one example, the composition can be completely devoid of ethoxylated castor oil. These ethoxylated castor oil concentrations, even formulations without ethoxylated castor oil, provide acceptable potency and drug delivery. Surprisingly, certain known permeation properties typically provided by ethoxylated castor oil, formulations that included higher concentrations of ethoxylated castor oil, e.g., 5 wt % as evaluated herein, did not exhibit adequate vasoconstriction and did not allow for effective delivery of the halobetasol propionate. Even with no ethoxylated castor oil, pharmaceutical compositions described herein can be prepared with superior vasoconstriction and delivery profiles. In one embodiment, the ethoxylated castor oil is present in an amount that provides acceptable mean scores resulting from VCA testing as described below. In another embodiment, the ethoxylated castor oil is present in an amount that provides mean scores resulting from VCA testing of the formulation that are at least 1.75, 2.0, 2.25, 2.5, or 2.75.

Turning now to the permeation enhancers, or more specifically, the MMPEs described herein, these compounds can be included in the pharmaceutical composition in various combinations of: N-lauroyl sarcosine, sodium octyl sulfate, methyl laurate, isopropyl myristate, oleic acid, glyceryl oleate, or sodium lauryl sulfoacetate. These compounds can be described herein as a "first compound" and a "second compound," and can include additional compounds as well. In one example, the combination of the first compound and the second compound can range from about 0.25 wt % to about 5 wt %. In another example, the combination of the first compound and the second compound can range from about 0.5 wt % to about 3 wt %. In yet another example, the combination of the first compound and the second compound can range from about 0.5 wt % to about 1 wt %. Each compound (of the first and second compound) can be individually present at from about 0.01 wt % to about 5 wt %, or from about 0.05 wt % to about 2 wt %, or from about 0.08 wt % to about 1 wt %, for example.

In one example, the first compound and the second compound can be present in the pharmaceutical composition at a weight ratio from about 1:2 to about 15:1. In one example, the first compound and the second compound can be present in the pharmaceutical composition 1:1 to 10:1. In another example, the first compound and the second compound can be present in the pharmaceutical composition at a weight ratio from about 1:2 to about 9:1. In yet another example, the first compound and the second compound can be present in the pharmaceutical composition at a weight ratio from about 1:2 to about 8:1; from about 1:2 to about 7:1; from about 1:2 to about 6:1; from about 1:2 to about 5:1; or about 1:2 to about 4:1; or about 1:2 to about 3:1, or about 1:2 to about 2:1; or about 1:1 to about 9:1, or about 5:1 to about 10:1, or about 8:1 to about 10:1, or at a ratio of about 1:1.

In one example of the pharmaceutical composition, the first compound can be methyl laurate and the second compound can be oleic acid. This formulation can include from 0 wt % to 3 wt % ethoxylated castor oil, from 0 wt % to 2 wt % ethoxylated castor oil, from 0 wt % to 1 wt % ethoxylated castor oil, and can be substantially devoid of ethoxylated castor oil, or can be completely devoid of ethoxylated castor oil. Formulations having the combination of methyl laurate, oleic acid, and 5 wt % ethoxylated castor oil surprisingly failed during VCA testing of the examples set forth herein. This was also true of other similar formulations tested as described below, for example. Thus, it was found that the absence of ethoxylated castor oil (or including limited amounts) provided improved results over formulations with typical concentrations of ethoxylated castor oil, e.g., 5 wt % or more.

In one example, the methyl laurate and the oleic acid can be present at a weight ratio from about 2:1 to about 1:2. In another example, the methyl laurate and the oleic acid can be present at weight ratio of about 1:1. Ratios outside of this range can also be used provided they provide penetration of the active agent at therapeutically effective levels. As mentioned, in one example, the pharmaceutical composition including the methyl laurate and the oleic acid can exclude ethoxylated castor oil. In one example, a composition comprising methyl laurate and oleic acid can be devoid of sodium lauryl sulfoacetate.

In another example, the first compound can be sodium lauryl sulfoacetate and the second compound can be isopropyl myristate. This formulation can include from 0 wt % to 3 wt % ethoxylated castor oil, from 0 wt % to 2 wt % ethoxylated castor oil, from 0 wt % to 1 wt % ethoxylated castor oil, can be substantially devoid of ethoxylated castor oil, or can be completely devoid of ethoxylated castor oil. In one example, the sodium lauryl sulfoacetate and the isopropyl myristate can be present at a weight ratio from about 5:1 to about 15:1. In another example, the sodium lauryl sulfoacetate and the isopropyl myristate can be present at a weight ratio from about 1:1 to about 10:1. In yet another example, the sodium lauryl sulfoacetate and the isopropyl myristate can be present at a weight ratio from about 8:1 to about 10:1. In a further example, the sodium lauryl sulfoacetate and the isopropyl myristate can be present at the weight ratio of about 9:1. Ratios outside of this range can also be used provide they provide penetration of the active agent at therapeutically effective levels. As mentioned, in one example, the pharmaceutical composition including the sodium lauryl sulfoacetate and the isopropyl myristate can exclude ethoxylated castor oil.

In another example, the first compound can be sodium lauryl sulfoacetate and the second compound can be oleic acid. This formulation can include from 0 wt % to 3 wt % ethoxylated castor oil, from 0 wt % to 2 wt % ethoxylated castor oil, from 0 wt % to 1 wt % ethoxylated castor oil, can be substantially devoid of ethoxylated castor oil, or can be completely devoid of ethoxylated castor oil. In one example, the sodium lauryl sulfoacetate and the oleic acid can be present at a weight ratio from about 5:1 to about 15:1. In another example, the sodium lauryl sulfoacetate and the oleic acid can be present at a weight ratio from about 1:1 to about 10:1. In yet another example, the sodium lauryl sulfoacetate and oleic acid can be present at a weight ratio of about 8:1 to about 10:1. In another example, the sodium lauryl sulfoacetate and the oleic acid can be present at a weight ratio of about 9:1. Ratios outside of this range can also be used provided they provide penetration of the active agent at therapeutically effective levels. As mentioned, in one example, the pharmaceutical composition including the sodium lauryl sulfoacetate and the oleic acid can exclude ethoxylated castor oil.

Further examples of the first compound and the second compound in the pharmaceutical composition can include (in either order): methyl laurate and isopropyl myristate; methyl laurate and oleic acid; methyl laurate and glyceryl oleate; methyl laurate and sodium lauryl sulfoacetate; isopropyl myristate and oleic acid; isopropyl myristate and glycerol oleate; isopropyl myristate and sodium lauryl sulfoacetate; oleic acid and glycerol oleate; oleic acid and sodium lauryl sulfoacetate; and glycerol oleate and sodium lauryl sulfoacetate, for example. Notably, disclosure of pairings of the "first compound" and the "second compound" can be interchangeable as it relates to weight ratios disclosed herein unless they are specifically described in an example. Thus, the compound listed as the "first compound" in a general pairing can be the "second compound" and the compound listed as the "second compound" in a general pairing herein can be the "first compound" with respect to weight ratio disclosure described herein. In one example, the composition can be devoid of sodium lauryl sulfoacetate.

In some examples, the pharmaceutical composition can include a third compound. The third compound can be N-lauroyl sarcosine, sodium octyl sulfate, methyl laurate, isopropyl myristate, oleic acid, glyceryl oleate, or sodium lauryl sulfoacetate. The third compound is not the same as the first compound and the second compound.

The pharmaceutical compositions described herein can be formulated with additional excipients. For example, the formulations can contain solvents such as isopropyl alcohol, di-isopropyl adipate, hexylene glycol, and/or water, as well as, buffers, such as, citric acid buffers, and sodium citrate, dihydrate.

Without being bound by theory, it is believed that combinations of ingredients as a whole, in some formulations, can impart superior properties related to stability and/or VCA testing. In one embodiment, the pharmaceutical composition can demonstrate improved stability. In another embodiment, the pharmaceutical composition can demonstrate superior potency as tested by vasoconstriction assay (VCA). In yet another embodiment, the pharmaceutical composition can demonstrate improved stability and superior potency as tested by VCA.

The pharmaceutical compositions described herein can have increased potency of active agent, such as halobetasol propionate, into or through the skin when compared to a comparative formulation devoid of the first and second compound (the MMPEs) and having an equivalent wt % of water replacing the MMPEs. The increase in penetration of the halobetasol propionate, in some examples, can be at least 5%, at least 10%, at least 20%, at least 30%, at least 40%, at least 50%, at least 60%, at least 70%, at least 80%, at least 90%, at least 100%, at least 250%, at least 500%, at least 750%, at least 1,000%, at least 1250%, at least 1500%, at least 2,000%, at least 3,000%, at least 4000% or even at least 8,000% greater than the penetration of the comparative formulation at a given period of time during the application, e.g. 4 hours, 24 hours etc. This increased penetration enhancement can also lead to a reduction in the total concentration of other ingredients that may be potential skin irritants in a formulation. In some embodiments, it has also been found that the presence of the MMPEs do not negatively affect the stability of the active ingredient in the formulation and/or the physical stability of the formulation.

Incorporating the first compound and the second compounds into the pharmaceutical compositions can also improve the physical and/or chemical stability of the pharmaceutical compositions. In general, long storage periods can result in active degradation, changes in pH, and changes in viscosity. In certain embodiments, the pharmaceutical compositions presented herein, can exhibit improved chemical and/or physical stability when stored, when compared to a comparative formulation devoid of the first compound and the second compound and having an equivalent amount of water added thereto in place of the first compound and the second compound.

In one example, the pharmaceutical composition can be chemically and/or physically stable for 9 months when stored at 25° C. In another example, the pharmaceutical composition can be chemically and/or physically stable for 6 months when stored at 25° C. In yet another example, the pharmaceutical compositions can be chemically and/or physically stable for 12 months when stored at 25° C. In a further example, the pharmaceutical compositions can be chemically and/or physically stable for 15 months, 18 months, 21 months, or even 24 months, when stored at 25° C.

In another example, the pharmaceutical composition can be chemically and/or physically stable for 3 months when stored at 40° C. In yet another example, the pharmaceutical composition can be chemically and/or physically stable for 6 months when stored at 40° C. In a further example, the pharmaceutical composition can be chemically and/or physically stable for 9 months when stored at 40° C.

In some examples, the formulation has an improved chemical profile relating to degradation products, i.e. fewer degradation products. Specific relative retention times (RRT) can be used to quantify this improved profile. Certain preparations can be used as a baseline to evaluate whether there is improvement in RRT. For example, RRT can correlate to degradation products of the halobetasol propionate (or other compounds). Relative retention time can be essentially an expression of a sample retention time in a high performance liquid chromatography column (HPLC) relative to more standard solutions carrying the same compound of interest. The magnitude (size) of the peak of a specific RRT relates to the amount of the degradation product present in the test sample. The presence of fewer degradation products can be associated with improved chemical stability. Thus, a change in the size of a peak correlates with the amount of a specific degradation product related to the compound. In accordance with the present disclosure, relative retention time of a degradation product related to halobetasol propionate can be measured at RRT 0.76-0.77, for example.

In one example, the degradation product observed at a specific relative retention time of the halobetasol propionate is not detected (N/D) in the pharmaceutical formulation, this can indicate that the product is free of the degradation product of halobetasol propionate. In another example, there is no degradation product observed at a specific relative retention time of 0.76-0.77 for the halobetasol propionate following 3 months, 6 months, or 9 months of long term storage conditions. In another example, the level of a degradation product observed at a specific relative retention time of the halobetasol propionate in the pharmaceutical composition is lower by at least each of the following: 5%, 10%, 20%, 30%, 40%, 50%, 60%, 70%, 80%, 90%, or 95% (when compared to the level of a degradation product observed at the same, specific relative retention time of halobetasol propionate in a comparable formulation). The level of the degradation product can be tested at about 1 month, about 3 months, about 6 months, about 9 months, about 12 months, about 15 months, about 18 months, about 21 months, or even about 24 months at long term and/or accelerated conditions. The comparable formulation can be a composition that does not incorporate the first compound and the second compound. Alternately, the comparable formulation can be a composition that includes a different first compound and a different second compound than a composition that includes methyl laurate and oleic acid as the first compound and the second compound. The improvements in the chemical and/or physical stability can also be manifested as improvements in the pH and viscosity of the formulations. In some examples, the pH of the formulation can be stable for at least about 3 months, about 6 months, about 9 months, about 12 months, about 15 months, about 18 months, about 21 months, or even about 24 months.

In other examples, the improved physical and/or chemical stability of the pharmaceutical composition can lead to increased commercial shelf life. In one example, pharmaceutical composition can have an increased shelf life of about 3 months, about 6 months, about 9 months, or about 12 months when compared to a comparative formulation devoid of the first compound and the second compound stored under the same conditions. In another example, the shelf life of the pharmaceutical composition can be at least about 27 months, at least about 30 months, at least about 33 months, or at least about 36 months.

In some examples, the pharmaceutical composition can include additional components. Examples of additional compounds that can be included in the pharmaceutical compositions can include water, thickening agents, gelling and/or solidifying polymers, emollients/surfactants excipients, fatty acid esters, parabens, solvents, buffers, and/or the like.

In one embodiment, the topical formulation can include water, and in some cases, water can be the ingredient that is present at the single greatest concentration. In one example, the water can range from about 30 wt % to about 60 wt %. In another example, the water can range from about 40 wt % to about 55 wt %. In some examples, the water can be deionized, purified, filtered, and/or pharmaceutical grade.

In another example, the pharmaceutical composition can include a solvent. In one example, the solvent can be selected from isopropyl alcohol, di-isopropyl adipate, hexylene glycol, hexylene glycol monoethyl ether, water, or a combination thereof. In another example, the solvent can be di-isopropyl adipate, hexylene glycol, and water. The pharmaceutical compositions can include isopropyl alcohol. In one example, the isopropyl alcohol can be present in the formulation between about 1 wt % to about 45 wt %. In another example, the isopropyl alcohol can be present from about 20 wt % to about 40 wt %. In a further example, the isopropyl alcohol can be present from about 30 wt % to about 40 wt %. In one example, the isopropyl alcohol can be present at about 35 wt %. Additionally, the topical formulation can include di-isopropyl adipate and/or hexylene glycol. In one example, the di-isopropyl adipate can be present in the formulation between about 1 wt % to about 10 wt %. In another example, the di-isopropyl adipate can be present from about 2 wt % to about 5 wt %. In one example, the hexylene glycol can be present in the formulation between about 1 wt % to about 15 wt %. In another example, the hexylene glycol can be present from about 5 wt % to about 10 wt %. In some examples, the solvents (including water) can be collectively be present in the composition from about 50 wt % to about 99 wt %. In another example, the solvents (including water) can be collectively greater than about 75 wt % of the composition.

In some examples, the composition can further include a buffer. In one example the buffer can be selected from the group consisting of citric acid, sodium citrate (including sodium citrate dihydrate), or a combination thereof. In one example, the composition can include citric acid and the citric acid can be present from about 0.01 wt % to about 2 wt %. In another example, the citric acid can be present from about 0.05 wt % to about 1 wt %. In one example, the composition can include sodium citrate and the sodium citrate can be present from about 0.01 wt % to about 2 wt %. In another example, the sodium citrate can be present from about 0.05 wt % to about 1 wt %. In one example, the buffers in the composition can collectively comprise from about 0.01 wt % to about 1 wt % of the composition. In yet another example, the buffers can collectively comprise from about 0.01 wt % to about 0.5 wt % of the composition.

In one example, the pharmaceutical composition can include halobetasol propionate, diisopropyl adipate, hexylene glycol, methyl laurate, and oleic acid. These components can be as described above. In one more specific example, a pharmaceutical composition having these components can have no degradation product observed at a relative retention time of 0.76 to 0.77 for the halobetasol propionate when tested following about 3 months, about 6 months, or about 9 months of long term storage. In one example, a pharmaceutical composition having these components can have a mean score resulting from vasoconstriction (VCA) testing of at least 2. In some embodiments, the pharmaceutical composition can further include additional components. In one example, the additional components can be isopropyl alcohol, water, or a combination thereof. In another example, the additional components can include buffers, as identified above. Any of the components in the composition can be as described above.

Any of the compositions described above can include other suitable carriers or excipients that may be used in the pharmaceutical compositions discussed herein are known in the art and can include, but are not limited to, solubilizers such as $C_2$ to $C_8$ straight and branched chain alcohols, diols and triols, moisturizers and humectants such as glycerin, amino acids and amino acid derivatives, poly-amino acids and derivatives, pyrrolidone carboxylic acids and their salts and derivatives, surfactants such as sodium laureth sulfate, sorbitan monolaurate, emulsifiers such as cetyl alcohol, stearyl alcohol, thickeners such as methyl cellulose, ethyl cellulose, hydroxymethyl-cellulose, hydroxypropyl-cellulose, polyvinyl-pyrrolidone, polyvinyl alcohol, and acrylic polymers.

In some examples, the pharmaceutical composition can be devoid of additional actives (e.g. single active formulation) or, alternately, can include a second active agent. In one example, the pharmaceutical composition can include one or more additional active agents selected from retinoids (e.g. tretinoin, adapalene, tazarotene, among others), vitamins, vitamin D, vitamin analogs, JAK inhibitors, kinase inhibitors, phosphodiesterase inhibitors, coal tar and coal tar extracts, keratolytics and combinations thereof.

The pharmaceutical compositions can also include one or more skin care actives. "Skin care actives" means all compounds or substances now known or later demonstrated to provide benefit when applied to skin and all compounds now claimed or in the future claimed to provide benefit when applied to skin. Skin care actives can provide benefits, or claimed benefits, in areas such as one or more of wrinkle removal or wrinkle reduction, firming of skin, exfoliation of skin, skin lightening, treatment of dandruff, treatment of acne, skin conditioning, development of tans and artificial tans, improvement of skin moisture content, improvement of skin barrier properties, control of sweat, anti-aging, reduction or avoidance of irritation, and reduction or avoidance of inflammation. Examples of skin care actives can include molecules such as peptides, proteins, oligonucleotides, fullerenes as well as small molecules. Skin care actives can be protease and/or enzyme inhibitors, anti-coenzymes, chelating agents, antibodies, antimicrobials, humectants, vitamins, skin protectants, antioxidants and/or skin soothing agents, plant extracts and the like. Examples of skin care actives can include but are not limited to vitamin C, vitamin E (alpha tocopherol), retinoids, soy derivatives (e.g. isoflavones), green tea polyphenols, alpha hydroxy acids (e.g. glycolic and lactic acids), beta hydroxy acids (e.g. salicylic acid), poly hydroxy acids, alpha lipoic acid, hemp oil (glycerides), niacinamide, dimethyl amino ethanol, coenzyme Q10, kinetin (plant growth hormone), dimethyl sulfone, and botulinum toxin.

The pharmaceutical compositions herein can be formulated as liquids, solutions, emulsions, creams, lotions, suspensions, triturates, gels, jellies, foams, pastes, sprays, ointments, shampoos, adhesives, traditional patches, or the like. In one example, the pharmaceutical compositions can be formulated as a topical spray. In one example, the topical spray can be a non-foamable, liquid spray. In another example, the formulation can be foamable. In one example, a foamable formulation can include a foam booster. In another example, the formulation is not a foam. In another embodiment, the formulation is a solution devoid of foaming agents or foam boosters.

The pharmaceutical compositions described herein can be used to treat various skin conditions. In one example, the skin condition can be dermatitis, sunburn, plaque dermatitis, eczema, allergy, skin rash, psoriasis, or plaque psoriasis. In another example, the skin condition can be plaque dermatitis, eczema, allergy, skin rash, psoriasis, or plaque psoriasis. In yet another example, the skin condition can be plaque psoriasis. In yet another example, the skin condition can be sunburn. In some examples, the treatment can be prophylactic.

The pharmaceutical compositions can be formulated as a topical spray and the step of applying the pharmaceutical composition can include spraying the pharmaceutical composition onto the skin surface of a subject. In another example, the pharmaceutical compositions can be formulated as a foam and the step of applying the pharmaceutical composition can include spreading the pharmaceutical composition onto the skin surface of a subject.

The pharmaceutical compositions can be applied to the skin of a subject and the potency assessed by vasoconstriction assay (VCA) testing. Visual assessment of skin blanching is the standard measurement tool employed in the vasoconstriction assay (VCA). In general, the vasoconstrictor assay can be considered one of the most widely used surrogate test to assess the potency of topical corticosteroids, and has been shown to correlate reasonably well with the clinical efficacy of corticosteroid formulations although it is not the mechanism by which efficacy is obtained (i.e., efficacy is a function of the drug's anti-inflammatory, immunosuppressive, or anti-mitotic properties). The results of the VCA have been used to a) classify topical corticosteroids into seven potency classes (Class I through VII) and b) identify and optimize new formulations for clinical development.

The primary efficacy variable for VCA testing is the amount of skin blanching assessed visually approximately 18 (±1) hours after test article applications. This assessment is typically performed with the subject standing with extended forearms side-by-side, slightly above hip level, with the ventral surfaces directed forward and slightly upward toward the evaluator. The assessment is performed under standard clinic lighting conditions.

The evaluator assesses the test sites and reports one integer score for each test site using the following scale:

0=No blanching; no change from surrounding area

1=Mild blanching; slight or indistinct outline at application site

2=Moderate blanching; discernible outline at application site

3=Marked blanching; distinct outline at application site

Each subject receives a score on the four-point scale (0-3) for each of the test formulations and the individual results for each formulation are then summed to obtain a "SUM" VCA score for each formulation. The "SUM" VCA score is then divided by the number of subjects to obtain a "MEAN" VCA score for each formulation. The "SUM" VCA score and the "MEAN" VCA score will be in the range of 0-3 with 0 being the lowest possible score (no visible effect) and 3 being the maximum possible score (highest possible effect).

Halobetasol propionate has been classified as a super high (superior) potency corticosteroid, whereas, triamcinolone acetonide is a corticosteroid that has been classified as having intermediate potency. Ultravate® cream (Ranbaxy) contains 0.05% halobetasol propionate. In one embodiment, the pharmaceutical compositions of the invention can be applied to the skin of a subject and the potency assessed by vasoconstriction assay (VCA) testing. In another embodiment, the mean score resulting from VCA testing of the pharmaceutical composition of the present invention can be greater than 1.5, 1.6, 1.7, 1.8, 1.9, 2.0, 2.1, 2.2, 2.3, 2.4, 2.5, 2.6, 2.7 or 2.8. In another embodiment, the mean score resulting from VCA testing of the pharmaceutical composition of the present invention can be equal to the mean score resulting from testing a comparative formulation. In a further embodiment, the mean score resulting from VCA testing of the pharmaceutical composition of the present invention can be greater than the mean score resulting from VCA testing of a comparative formulation. In one embodiment, the comparative formulation can be Ultravate® cream (Ranbaxy) containing 0.05% halobetasol propionate. In another embodiment, the comparative formulation can be a formulation containing triamcinolone acetonide cream, 0.5% (E. Fougera & Co.).

Embodiments of the present disclosure will be described with reference to the following Examples which are provided for illustrative purposes only and should not be used to limit the scope of or construe the invention.

EXAMPLES

Example 1

Vasoconstriction (VCA) Studies

Several formulations were prepared to establish various solvent combinations for the vasoconstriction properties for the pharmaceutical composition described herein. The formulations included an active agent, along with various solvent, penetration enhancers and buffer combinations, as set forth in Table 1.

TABLE 1

Formulations for VCA Testing

| Ingredient (w/w) | C1 | C2 | C3 | C4 | C5 | Vehicle I |
|---|---|---|---|---|---|---|
| Halobetasol Propionate | 0.05 | 0.05 | 0.05 | 0.05 | 0.05 | — |
| Isopropyl Alcohol | 35 | 35 | 35 | 35 | 35 | 35 |
| Di-isopropyl Adipate | 3 | 3 | 3 | 3 | 3 | 3 |
| Hexylene Glycol | 7.5 | 7.5 | 7.5 | 7.5 | 7.5 | 7.5 |
| Citric Acid, anhydrous | 0.09 | 0.09 | 0.09 | 0.09 | 0.09 | 0.09 |
| Sodium Citrate, dihydrate | 0.07 | 0.07 | 0.07 | 0.07 | 0.07 | 0.07 |
| Purified Water | 47.79 | 47.79 | 47.29 | 47.29 | 47.29 | 44.84 |
| Polyoxyl 35 castor Oil | 5 | 5 | 5 | 5 | 5 | 5 |
| Methyl Laurate | 0.5 | 0.5 | — | — | — | 0.5 |
| Isopropyl Myristate | — | — | 1 | — | — | 1 |
| Oleic Acid | 1 | — | — | 1 | — | 1 |
| Glyceryl Oleate | — | — | — | — | 1 | 1 |
| Sodium Lauryl Sulfoacetate | — | 1 | 1 | 1 | 1 | 1 |
| Total | 100 | 100 | 100 | 100 | 100 | 100 |

Batches of the formulations in Table 1 were prepared using a laboratory mixer. The organic phase (isopropyl alcohol, di-isopropyl adipate, hexylene glycol) was prepared in the mixer vessel. An aqueous phase (purified water, anhydrous citric acid, di-hydrate sodium citrate, and where applicable, sodium lauryl sulfoacetate) was prepared in a separate container and then added to the organic phase. Finally, the oil phase containing polyoxyl 35 castor oil, and where applicable, methyl laurate, isopropyl myristate, oleic acid and/or glyceryl oleate was prepared and incorporated into the formulations. The composition was gently mixed using a mixer to ensure complete dissolution after each addition. The formulations were packaged in 60 mL amber glass bottles and capped with a polytetrafluoroethylene liner.

In addition to the formulations in Table 1 above, commercially available formulations (i.e., Ultravate® cream (Ranbaxy) and Triamcinolone acetonide cream, 0.5% (E. Fougera & Co.)) were also tested for their vasoconstriction (VCA) values. Ultravate® cream contains 0.05% halobetasol propionate and thus contains the same active at the same concentration as the formulations in Table 1. Halobetasol propionate is classified as a super high potency corticosteroid whereas triamcinolone acetonide is a corticosteroid with intermediate potency.

More specifically, in order to test the vasoconstriction properties of these formulations and the comparable compositions, forty subjects (16 males/24 females) applied the formulation for a 16 hour period. Vasoconstriction testing was analyzed according to the following protocol. On Day 1, eight~1 $cm^2$ test sites were identified on the ventral forearms of the subject (4 test sites on each forearm). A single application of approximately 10 mg of each test article was applied to the designated test site in accordance with a computer-generated randomization code, thus blinding the evaluator to the application sequence. Five novel HBP solutions (identified above as C1-C5), 0.05% formulations, as well as the two reference products, and vehicle I were evaluated. All of the treatments were applied in the late afternoon (e.g., at approximately 4:00 pm) on Day 1; then, the test sites on each arm were protected using a raised perforated guard by securing the guards to the arms with a non-occlusive tape, and the subjects were scheduled for follow-up on the following day. Subjects were instructed to keep the test sites dry for 16 hours after test article application, and then instructed to remove the protective guards and gently wash the test sites with mild soap and water.

Subjects were scheduled for follow-up so that the clinic visit was two hours after removal of the guards and washing (i.e., 18 hours after the test article applications or at 10:00 am based upon a 4:00 pm application time on Day 1). At the clinic, an experienced evaluator performed the visual assessment of vasoconstriction (skin blanching) based on a four-point scale (0-3). Safety was from local and systemic adverse events (AEs).

During the testing, none of the subjects had an active dermatitis, including sunburn. The subjects had not used a topical dermatological medication on their forearm within one month of the study and were not using any concurrent medications that might interfere with the study. The excluded medications included nitroglycerin, anti-hypertensives, anti-histamines, non-steroidal anti-inflammatory drugs, topical corticosteroids, systemic corticosteroids, and cold/cough products having anti-histamines, phentolamine, and pseudo-ephedrine. The VCA results were obtained and are reported in Table 2, as follows:

TABLE 2

VCA Results

| Formulation | VCA Score |
|---|---|
| C1 | 1.56 |
| C2 | 1.41 |
| C3 | 1.56 |
| C4 | 1.64 |
| C5 | 1.46 |
| Ultravate ® Ointment* | 2.95 |
| Triamcinolone Acetonide Cream | 1.46 |
| Vehicle I | 0.28 |

*Also known as Ultravate ® Cream

The VCA results for the halobetasol propionate containing compositions were not significantly different from one another and the triamcinolone acetonide cream. The Ultravate® ointment exhibited significantly higher VCA values than the compositions that contained the MMPEs and the polyoxyl 35 castor oil. Thus, the performance of all of the tested formulations (C1-C5) were inferior to the Ultravate® ointment despite the fact that all formulations contained 0.05% of the super high potency cortocosteroid halobetasol propionate. The tested formulations performed on a par with the mid potency triamcinolone acetonide cream.

It was proposed that one or more ingredients in the formulation may be incompatible with the API (active) or other excipients. Alternately, one or more ingredients in the formulation could be enhancing transdermal permeation to deeper tissues (local delivery of the API in the superficial tissue is reduced resulting in the lower than expected VCA scores) or impeding permeation (API is not being delivered into the skin and reducing the apparent potency of the formulation resulting in the lower than expected VCA scores). As such, the VCA compositions were reformulated as shown in Table 3 and re-tested for vasoconstriction. Adjustments were made to the concentration of MMPEs and polyoxyl 35 castor oil.

TABLE 3

Reformulated Compositions for VCA Testing

| Ingredient (w/w) | C6 | C7 | C8 | C9 | Vehicle II | C2 |
|---|---|---|---|---|---|---|
| Halobetasol Propionate | 0.05 | 0.05 | 0.05 | 0.05 | — | 0.05 |
| Isopropyl Alcohol | 35 | 35 | 35 | 35 | 35 | 35 |
| Di-isopropyl Adipate | 3 | 3 | 3 | 3 | 3 | 3 |
| Hexylene Glycol | 7.5 | 7.5 | 7.5 | 7.5 | 7.5 | 7.5 |
| Citric Acid, anhydrous | 0.09 | 0.09 | 0.09 | 0.09 | 0.09 | 0.09 |
| Sodium Citrate Dihydrate | 0.07 | 0.07 | 0.07 | 0.07 | 0.07 | 0.07 |
| Purified Water | 47.79 | 53.29 | 53.29 | 53.29 | 46.84 | 54.29 |
| Polyoxyl 35 Castor Oil | 5 | — | — | — | 5 | — |
| Methyl Laurate | 0.5 | 0.5 | — | — | 0.5 | — |
| Isopropyl Myristate | — | — | 0.1 | — | 0.1 | — |
| Oleic Acid | 1 | 0.5 | — | 0.1 | 1 | — |
| Sodium Lauryl Sulfoacetate | — | — | 0.9 | 0.9 | 0.9 | — |
| Total | 100 | 100. | 100 | 100 | 100 | 100 |

Batches of the formulations in Table 3 were prepared using a laboratory mixer. Formulations containing polyoxyl 35 castor oil were prepared as described above. For the remaining formulations, the organic phase (isopropyl alcohol, di-isopropyl adipate, hexylene glycol, and where applicable, methyl laurate, isopropyl myristate and/or oleic acid) was prepared in the mixer vessel. An aqueous phase (purified water, anhydrous citric acid, di-hydrate sodium citrate, and where applicable, sodium lauryl sulfoacetate) was prepared in a separate container and then added to the organic phase. The composition was gently mixed using a mixer to ensure complete dissolution after each addition. The formulations were packaged in 60 mL amber glass bottles and capped with a polytetrafluoroethylene liner.

In addition to the formulations in Table 3 above, commercially available formulations were also tested for their vasoconstriction (VCA) values (Ultravate® cream (Ranbaxy) and Triamcinolone acetonide cream, 0.5% (E. Fougera & Co.)). More specifically, in order to test the vasoconstriction properties of these modified formulations and the comparable compositions, 38 subjects (17 males/21 females) were enrolled in the study. Vasoconstriction testing was analyzed according to the protocol described above and results are shown in Table 4.

TABLE 4

VCA Results for Reformulated Compositions

| Formulation | Mean VCA Score |
|---|---|
| C8 | 2.83 |
| C7 | 2.72 |
| C9 | 2.67 |
| Ultravate ® Cream | 2.61 |
| C2 | 2.56 |
| C6 | 1.44 |

TABLE 4-continued

VCA Results for Reformulated Compositions

| Formulation | Mean VCA Score |
|---|---|
| Triamcinolone acetonide cream, 0.5% | 1.44 |
| Vehicle II | 0.17 |

Table 4 provides a tabular summary of the key study results which indicate generally that all 3 MMPE formulations (C8, C7, and C9) preformed better than the comparative commercial formulation, Ultravate® Cream. The base formulation that did not incorporate any MMPEs, the MMPE containing formulation that incorporated castor oil, vehicle II, and Triamcinolone acetonide cream, 0.5% performed worse than the Ultravate® cream. FIG. 1 graphically depicts these results. The higher VCA results for MMPE formulations were unexpected because the values observed in the previous VCA study for MMPE containing formulations (See compositions in Table 1 above and the VCA data in Table 2) were significantly lower. With specific respect to the low polyoxyl 35 castor oil VCA score, this was considered particularly unusual. Polyoxyl 35 castor oil is a non-ionic surfactant (emulsifying agent) that is often used to improve the solubilization of lipophilic drugs in oral, topical, parental, and cosmetic formulations. In addition, some data indicates that polyoxyl 35 castor oil can act as a hydrophilic penetration enhancer. Accordingly, the limiting effects of the polyoxyl 35 castor oil in these formulations are contrary to what might be expected.

Example 2

Stability Test

Stability testing was performed on several VCA formulations in Example 1 (Table 4, group A). Batches of formulations shown in Table 5 below were prepared at 2 kg scale using a laboratory mixer. An organic phase (halobetasol propionate, isopropyl alcohol, di-isopropyl adipate, hexylene glycol, and when applicable, the methyl laurate, isopropyl myristate, and oleic acid) was prepared in mini-Olsa mixer. An aqueous phase (purified water, anhydrous citric acid, di-hydrate sodium citrate, and where applicable, the sodium lauryl sulfoacetate) was then prepared in a separate container. The aqueous phase was then added to the organic phase.

With respect to all of the formulations, the compositions were gently mixed using a mixer to ensure complete dissolution after each addition. The formulations were packaged in 60 mL amber glass bottles and capped with a polytetrafluoroethylene liner.

TABLE 5

Stability Formulations Tested

| Ingredient (w/w) | C7 | C8 | C9 | C2 |
|---|---|---|---|---|
| Halobetasol Propionate | 0.05 | 0.05 | 0.05 | 0.05 |
| Isopropyl Alcohol | 35 | 35 | 35 | 35 |
| Di-isopropyl Adipate | 3 | 3 | 3 | 3 |
| Hexylene Glycol | 7.5 | 7.5 | 7.5 | 7.5 |
| Citric Acid, anhydrous | 0.09 | 0.09 | 0.09 | 0.09 |
| Sodium Citrate Dihydrate | 0.07 | 0.07 | 0.07 | 0.07 |
| Purified Water | 53.29 | 53.29 | 53.29 | 54.29 |
| Polyoxyl 35 Castor Oil | — | — | — | — |
| Methyl Laurate | 0.5 | — | — | — |
| Isopropyl Myristate | — | 0.1 | — | — |
| Oleic Acid | 0.5 | — | 0.1 | — |
| Sodium Lauryl Sulfoacetate | — | 0.9 | 0.9 | — |
| Total | 100 | 100 | 100 | 100 |

The formulations above in Table 5 were tested for physical and chemical stability in long term and accelerated storage conditions. Long term storage conditions were 25° C.±2° C. and 60%±5% relative humidity with bottles stored in an upright vertical orientation for 0, 3, 6, and when possible, 9, 12, 18, and 24 months. Accelerated storage conditions were 40° C.±2° C. and 75%±5% relative humidity, with bottles stored in an upright vertical orientation, for 0, 1, 3, and 6 months.

The stability assessments included monitoring the visual appearance, viscosity, pH, isopropyl alcohol assay, active identification, API assay for the halobetasol propionate, and degradation products.

TABLE 6

Long Term Storage Results

| Formulation | Time Period (months) | Assay (w/w %) | Assay (%) | Impurities (%) RRT 0.76-0.77 |
|---|---|---|---|---|
| C7 | T0 | 0.049 | 98 | N/D |
|  | T3 | 0.048 | 96 | N/D |
|  | T6 | 0.049 | 99 | N/D |
|  | T9 | 0.049 | 98 | N/D |
| C8 | T0 | 0.049 | 98 | N/D |
|  | T3 | 0.048 | 96 | 0.11 |
|  | T6 | 0.050 | 99.5 | 0.16 |
|  | T9 | 0.049 | 98 | 0.17 |
| C9 | T0 | 0.048 | 97 | N/D |
|  | T3 | 0.048 | 95 | N/D |
|  | T6 | 0.049 | 97 | 0.15 |
|  | T9 | 0.048 | 96 | 0.22 |
| C2 | T0 | 0.048 | 96 | N/D |
|  | T3 | 0.047 | 93 | 0.088 |
|  | T6 | 0.048 | 96 | 0.17 |
|  | T9 | 0.048 | 96 | 0.27 |

N/D above indicates that no impurities were detected and the HBP did not degrade in the formulation.

Based on the results shown in Table 6 above, C7 exhibited the most chemical stability in the long term storage conditions. The RRT (relative retention time) at 0.76-0.77 of C7 was not detectable (N/D) at 9 months. Thus, C7 demonstrated superior chemical stability. It is noted that the base formulation C2, excluding MMPEs, exhibited increasing degradation at 3 months, 6 months, and 9 months storage.

TABLE 7

Accelerated Storage Results

| Formulation | Time Period (months) | Assay (w/w %) | Assay (%) | Impurities (%) RRT 0.76-0.77 |
|---|---|---|---|---|
| C7 | T0 | 0.049 | 98 | N/D |
|  | T1 | N/AV | N/AV | 0.20 |
|  | T3 | 0.048 | 95 | 0.67 |
|  | T6 | 0.048 | 96.5 | 1.26 |
| C8 | T0 | 0.049 | 98 | N/D |
|  | T1 | N/AV | N/AV | 0.30 |
|  | T3 | 0.048 | 95 | 1.07 |
|  | T6 | 0.049 | 97 | 1.96 |
| C9 | T0 | 0.048 | 97 | N/D |
|  | T1 | 0.048 | 96 | 0.26 |
|  | T3 | 0.046 | 93 | 0.95 |
|  | T6 | 0.048 | 95 | 1.71 |
| C2 | T0 | 0.048 | 96 | N/D |
|  | T1 | 0.047 | 95 | 0.32 |
|  | T3 | 0.046 | 92 | 1.05 |
|  | T6 | 0.047 | 94 | 1.97 |

N/D above indicates that no impurities were detected and the HBP did not degrade in the formulation.

Based on the results shown in Table 7 above, formulation C7 exhibited the most chemical stability in the accelerated storage conditions. The RRT at 0.76-0.77 of C7 was 1.26 at 6 months. Thus, C7 demonstrated the best chemical stability.

TABLE 8

Summary of Impurity Results RRT 0.76

| Formulation | Time Zero | 9 Months at 25° C. | 1 Month at 40° C. | 6 Months at 40° C. |
|---|---|---|---|---|
| C7 | ND | ND | 0.20 | 1.26 |
| C8 | ND | 0.17 | 0.30 | 1.96 |
| C9 | ND | 0.22 | 0.26 | 1.71 |
| C2 | ND | 0.27 | 0.32 | 1.97 |

HBP assay values were generally consistent after 9 months storage at 25° C. and 6 months storage at 40° C. There was little to no observable decrease in assay values. The pH and viscosity results were generally consistent under both long term and accelerated storage conditions.

It will be readily apparent to those skilled in the art that various changes and modifications of an obvious nature may be made without departing from the spirit of the invention, and all such changes and modifications are considered to fall within the scope of the invention as defined by the appended claims. Such changes and modifications would include for example, adding additional ingredients to the compositions described herein. Many additional modifications and variations of the embodiments described herein may be made without departing from the scope, as is apparent to those skilled in the art. The specific embodiments described herein are offered by way of example only.

What is claimed is:

1. A pharmaceutical composition comprising:
   0.01-10 wt % halobetasol propionate;
   1-45 wt % isopropyl alcohol;
   1-10 wt % di-isopropyl adipate;
   1-15 wt % hexylene glycol;
   30-60 wt % water;
   0.01-5 wt % methyl laurate;
   0.01-5 wt % oleic acid;

0.01-2 wt % citric acid; and 0.01-2 wt % sodium citrate (dihydrate), wherein the composition is devoid of ethoxylated castor oil.

2. The pharmaceutical composition of claim 1, formulated as a topical spray.

3. The pharmaceutical composition of claim 1, wherein no degradation product is observed at a relative retention time of 0.76-0.77 for the halobetasol propionate following 3 months of storage at long term conditions of 25° C.±2° C. and 60%±5% relative humidity.

4. The pharmaceutical composition of claim 1, wherein no degradation product is observed at a relative retention time of 0.76-0.77 for the halobetasol propionate following 6 months of storage at long term conditions of 25° C.±2° C. and 60%±5% relative humidity.

5. The pharmaceutical composition of claim 1, wherein no degradation product is observed at a relative retention time of 0.76-0.77 for the halobetasol propionate following 9 months of storage at long term conditions of 25° C.±2° C. and 60%±5% relative humidity.

6. The pharmaceutical composition of claim 1, wherein a mean score resulting from vasoconstriction testing is at least 2.

7. The pharmaceutical composition of claim 1, wherein a weight ratio of methyl laurate to oleic acid ranges from about 1:2 to about 15:1.

8. The pharmaceutical composition of claim 1, wherein a weight ratio of the methyl laurate to the oleic acid ranges from about 1:2 to about 2:1.

9. The pharmaceutical composition of claim 8, wherein the weight ratio is about 1:1.

10. The pharmaceutical composition of claim 1, wherein the halobetasol propionate ranges from about 0.25 wt % to about 2 wt %.

11. The pharmaceutical composition of claim 1, wherein the pharmaceutical composition is devoid of sodium lauryl sulfoacetate.

* * * * *